United States Patent [19]

Baker et al.

[11] Patent Number: 4,767,766

[45] Date of Patent: Aug. 30, 1988

[54] DERIVATIVES OF 3-HYDROXYAZABENZO(B)THIOPHENE USEFUL AS 5-LIPOXYGENASE INHIBITORS

[75] Inventors: Robert K. Baker; Kathleen M. Rupprecht, both of Cranford; Arsenio A. Pessolano, Colonia; Philippe L. Durette, New Providence, all of N.J.

[73] Assignee: Merck & Co., Inc., Rahway, N.J.

[21] Appl. No.: 8,881

[22] Filed: Jan. 30, 1987

[51] Int. Cl.$^4$ .................. A61K 31/435; C07D 495/04
[52] U.S. Cl. ..................................... 514/301; 546/114
[58] Field of Search ........................ 546/114; 514/301

[56] References Cited

U.S. PATENT DOCUMENTS 2,811,527 10/1957 Sheehan ............................. 546/114

OTHER PUBLICATIONS

Chem. Abst. vol. 34, 4737.

Gewald et al., J. Prakt. Chem. 316(6), pp. 1030–1036 (1974); Chem. Abst. 82, 72823m (1975).
Zhiryakov et al., Chem. Abst. vol. 63,13231d (1965).
Koenigs et al., Chem. Abst. vol. 22, 420 (1928).

*Primary Examiner*—M. C. Lee
*Assistant Examiner*—Bernard I. Dentz
*Attorney, Agent, or Firm*—Theresa Y. Cheng; Michael C. Sudol

[57] ABSTRACT

3-Hydroxyazabenzo[b]thiophene derivatives having optionally 2-aryl, 2-aralkyl, 2-alkyl or 2-alkenyl substituents were prepared by, among other methods, ring closure of an appropriately substituted benzylthio-alkoxycarbonyl-pyridine. These compounds are found to be useful in the treatment of pain, fever, inflammation, arthritic conditions, asthma, allergic disorders, skin diseases such as psoriasis and atopic eczema, cardiovascular disorders, inflammatory diseases and other leukotriene mediated diseases.

4 Claims, No Drawings

DERIVATIVES OF 3-HYDROXYAZABENZO(B)THIOPHENE USEFUL AS 5-LIPOXYGENASE INHIBITORS

BACKGROUND OF THE INVENTION

This invention relates to 3-hydroxyazabenzothiophenes having the 2-position substituted with an optionally substituted aryl, aralkyl, alkyl, or alkenyl group, for example, 3-acetyloxy-7-aza-2-phenyl-benzo[b]thiophene.

These novel azabenzothiophenes are found to be either specific 5-lipoxygenase inhibitors or dual 5-lipoxygenase/cyclooxygenase inhibitors and are therefore useful in the treatment of prostaglandin and/or leukotriene mediated diseases.

Among various potent biological mediators derived from the oxygenation of arachidonic acid, prostaglandins and leukotrienes have been linked to various diseases. Notably, the biosynthesis of prostaglandins has been identified as a cause of inflammation, arthritic conditions and pain, and the formation of leukotrienes has been connected to immediate hypersensitivity reactions and pro-inflammatory effects. It has been established that arachidonic acid undergoes oxygenation via two major enzymatic pathways:

(1) The pathway catalyzed by the enzyme cyclooxygenase; and
(2) The pathway catalyzed by the enzyme 5-lipoxygenase.

Interruption of these pathways by enzyme inhibition has been explored for effective therapy. For example, non-steroidal anti-inflammatory drugs (NSAID's) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof are believed to play an important role in causing inflammation (B. Samuelsson, *Science*, 220, 568 (1983); D. Bailey et al, *Ann. Rpts. Med. Chem.*, 17, 203 (1982)).

DETAILED DESCRIPTION OF THE INVENTION

A. SCOPE OF THE INVENTION

The present invention relates to novel compounds of formula (I):

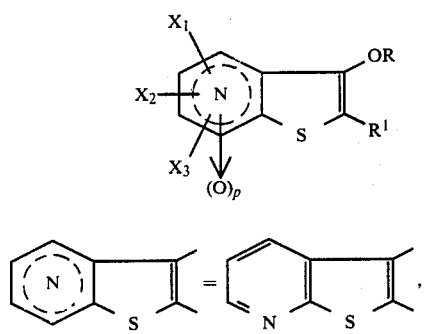

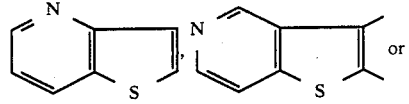

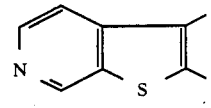

or a pharmaceutically acceptable salt thereof wherein N can be at carbon 4, 5, 6 or 7;

$X_1$, $X_2$ and $X_3$ independently are:

(1) Q, where Q is H; loweralkyl, especially $C_{1-6}$ alkyl; haloloweralkyl, especially fluoro or chloro $C_{1-6}$ alkyl such as trifluoromethyl; phenyl of formula

or naphthyl; or imidazole of formula

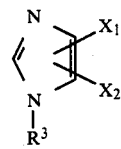

wherein $R^3$ is H, $C_{1-6}$ alkyl, $C_{6-14}$ aryl, $C_{3-6}$ cycloalkyl or halo $C_{1-6}$ alkyl;

(2) halo, especially chloro, fluoro, or bromo;
(3) loweralkenyl, especially $C_{2-6}$ alkenyl, such as ethenyl and allyl;
(4) loweralkynyl, especially $C_{2-6}$ alkynyl, for example, ethynyl or n-butynyl;

wherein q is an integer of 0 to 2;
(6) —OQ;
(7) —CHQCOQ$^1$, where Q$^1$ is Q and can be the same as or different from Q;
(8) —CHQ(CO)OQ$^1$;
(9) —CH$_2$SQ or —CHQSQ$^1$;
(10) —CH$_2$OQ or —CHQOQ$^1$;
(11) —COQ;
(12) —(CO)OQ;
(13) —O(CO)Q;
(14) —NQQ$^1$;
(15) —NQ(CO)Q$^1$;
(16) —NQSO$_2$Q$^1$;
(17) —SO$_2$NQQ$^1$;
(18) —SO$_3$Q
(19) —CN;
(20) —NO$_2$;
(21) —CONQQ$^1$;
(22) —NO;
(23) —CSQ;
(24) —CSNQQ$^1$;

(25) —CF$_2$SQ;
(26) —CF$_2$OQ;
(27) —NQCONHQ$^1$ or —NQCONQ$^1$Q$^2$; or
(28) -methylenedioxy;

R$^1$ is
(a) H;
(b) loweralkyl, especially C$_{1-6}$ alkyl, such as methyl, ethyl, i-propyl, n-propyl, t-butyl, n-butyl, i-pentyl, n-pentyl, and n-hexyl;
(c) aryl, especially C$_{6-14}$ aryl, e.g., naphthyl, anthryl, phenyl or substituted phenyl of formula

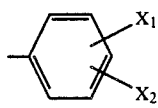

(d) lowercycloalkyl, especially C$_{3-6}$ cycloalkyl, e.g., cyclopropyl, cyclopentyl, and cyclohexyl;
(e) haloloweralkyl, especially halo C$_{1-6}$ alkyl, e.g. —CF$_3$, —CHF$_2$, —CF$_2$CF$_3$;
(f) heteroaryl or heteroaryl substituted with X$_1$ and X$_2$ especially pyridyl imidazolyl, pyrryl, furyl or thienyl wherein X$_1$ and X$_2$ are as previously defined;
(g) benzyl of formula

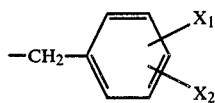

(h) loweralkynyl, especially C$_{1-6}$ alkynyl, such as HC≡C—; CH$_3$—C≡C—, or HC≡C—CH$_2$—;
(i) loweralkenyl, especially C$_{1-6}$ alkenyl, such as CH$_2$=CH—, CH$_3$CH=CH—, CH$_2$=CHCH$_2$—, CH$_3$CH=CH—CH$_2$—, (CH$_3$)$_2$C=CH— or —CH=CHCOOR$^2$ wherein R$^2$ is loweralkyl, especially C$_{1-6}$alkyl,
(j) aralkenyl of formula

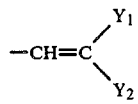

wherein Y$_1$ and Y$_2$ independently are phenyl and heteroaryl as previously defined;
(k) aralkynyl of formula

(l) (CH$_2$)$_m$(CO)R$^3$ wherein m is an integer of 1-6 and R$^3$ is H, C$_{1-6}$alkyl, C$_{6-14}$aryl, C$_{3-6}$cycloalkyl or haloC$_{1-6}$alkyl;
(m) —(CH$_2$)$_m$OR$^3$;
(n) —(CH$_2$)$_m$O(CO)R$^3$;
(o) —(CH$_2$)$_m$NR$^3$R$^4$ wherein R$^4$ can be the same or different from R$^3$ and R$^4$ is R$^3$;
(p) —(CH$_2$)$_m$—NR$^3$(CO)R$^4$;
(q) —(CH$_2$)$_m$(CO)OR$^3$; or
(r)

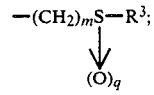

R is
(a) H;
(b) —(CO)R$^3$;
(c) —(CO)OR$^3$;
(d) —(CO)NR$^3$R$^4$;
(e) —(CO)SR$^3$;
(f) —(CH$_2$)$_m$COR$^3$;
(g) —(CH$_2$)$_m$OR$^3$;
(h) —(CH$_2$)$_m$O(CO)OR$^3$;
(i) —(CH$_2$)$_m$NR$^3$R$^4$;
(j) —(CH$_2$)$_m$NR$^3$(CO)R$^4$;
(k) loweralkyl as previously defined;
(l) lowercycloalkyl as previously defined; or
(m) haloloweralkyl as previously defined; and
p is 0 or 1.

Preferably, an enzyme inhibitor of this invention is of formula:

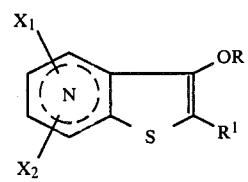

wherein X$_1$, X$_2$, R and R$^1$ are as previously defined.

More preferably, an enzyme inhibitor of this invention is of formula:

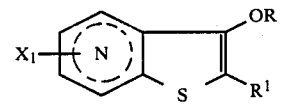

wherein
R is H or (CO)CH$_3$;
R$^1$ is phenyl substituted with X$_2$ or pyridyl;
X$_1$ is
(a) H;
(b) C$_{1-6}$alkyl;
(c) halo;
(d) halo-C$_{1-6}$-alkyl, e.g. CF$_3$;
(e) CN;
(f) —(CO)OR$^3$;
(g) —OC$_{1-6}$ alkyl;
(h) phenyl-CH(OH)—;
(i) CH$_2$S-Aryl; or
(j) —CH$_2$S—(CH$_2$)$_x$-aryl;
wherein x is 1 to 4;
X$_2$ is
(a) H:
(b) -methylenedioxy;
(c) halo-C$_{1-6}$alkyl, e.g., CF$_3$;
(d) halo;
(e) CN;
(f) —OC$_{1-6}$alkyl;
(g) —OC$_{1-6}$alkylphenyl;
(h) —(CO)OR$^3$;
(i) C$_{1-6}$alkyl; or (g) NO₂. B. Preparation of the compounds of the invention The compounds of the present invention can be divided into four subclasses depending upon the position of the aza substitution in the benzo[b] thiophene ring (position 4, 5, 6, or 7). General procedures, specific examples, and tables of physical data are given below.

I. 2-ARYL—7-AZA—BENZO[b]THIOPHENES

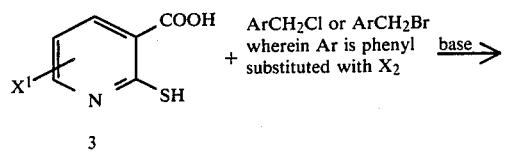
(a)

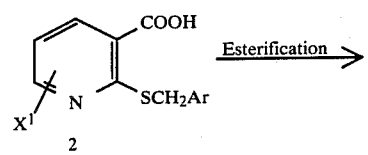

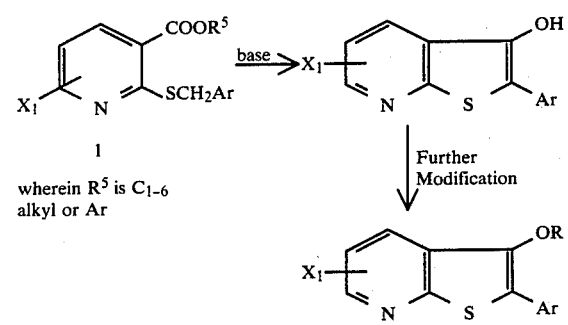

wherein R⁵ is C₁₋₆ alkyl or Ar

Compounds of this subclass are prepared by base-catalyzed (sodium hydride, potassium t-butoxide, lithium diisopropylamide, or the like) ring closure of an appropriately substituted alkyl or benzyl 2-arylmethylthionicotinate, for example, compound 1 in a solvent, such as dimethylsulfoxide, N,N-dimethylformamide, N-methylpyrrolidinone, tetrahydrofuran, or the like, at a temperature of from ambient to 100° C. for a period of six to twenty-four hours. The required alkyl or benzyl 2-arylmethylthionicotinates (1) are prepared by base-catalyzed (cesium carbonate, diazabicyclo[5,4,0]undec-7-ene(DBU), triethylamine, or the like) esterification of an appropriately substituted 2-arylmethylthionicotinic acid in a solvent such as acetonitrile, tetrahydrofuran, N,N-dimethylformamide, or the like in the presence of a slight excess of alkyl chloride, bromide, or iodide or benzyl chloride or bromide, at a temperature of from ambient to 65° C. for a period of six to twenty-four hours. The methyl nicotinates may also be prepared by treatment with carbonyldiimidazole in a solvent such as N,N-dimethylformamide followed by treatment with sodium methoxide in methanol. The required 2-arylmethylthionicotinic acids (2) are prepared by treatment of the known nicotinic acids (3) with two equivalents of base, such as sodium methoxide in methanol, sodium hydride in N,N-dimethylformamide, or potassium t-butoxide in tetrahydrofuran or the like, at a temperature of from −5° to 25° C. followed by treatment with the appropriately substituted arylmethyl chloride or bromide at ambient temperatures for a period of time from one to 24 hours.

As shown below in scheme (b), selective modification of the 6-position of the pyridine ring, when it is appropriate, can be obtained by treatment of a 2-aryl-3-methoxymethoxy-7-azabenzo[b]thiophene with a nucleophile, such as n-butyllithium or t-butyllithium, in a solvent such as tetrahydrofuran at a temperature from −78° C. to room temperature for 1–24 hours. Alternatively, as shown in scheme (c), modification can be effected by lithiation of the 6-position with a non-nucleophilic base such as trityllithium, followed by treatment with an electrophile, such as benzaldehyde.

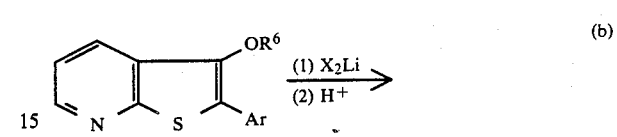
(b)

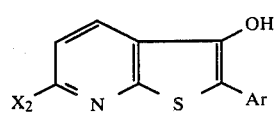

wherein R⁶ is an acid-removable protecting group, e.g. —CH₂OCH₃; X₂ and Ar are as previously defined.

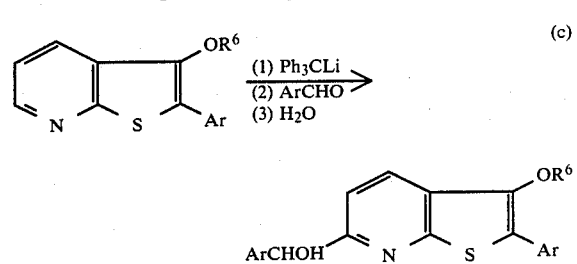
(c)

Substitution in the pyridine ring is also effected via oxidation of the 3-acetyloxy-2-arylbenzo[b]thiophene derivatives (4) to their corresponding N-oxides (5) by treatment with an oxidizing agent, such as m-chloroperbenzoic acid or the like in a solvent such as dichloromethane, tetrahydrofuran, or the like at a temperature of from ambient to 65° C. for a period of time of from one to 24 hours.

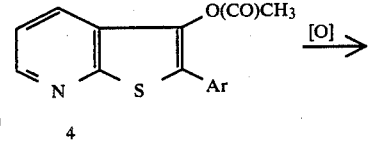

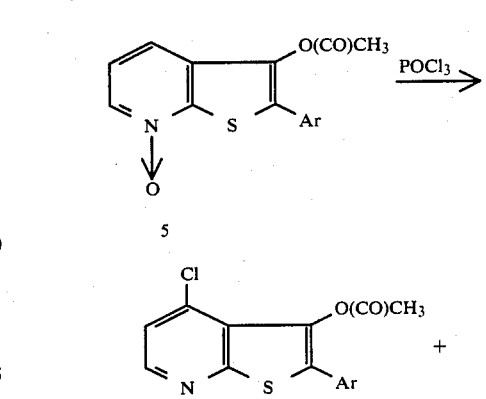

-continued

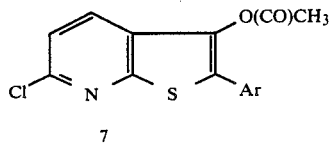

7

Treatment of the pyridine N-oxide derivatives (5) with an acid chloride, such as phosphoryl chloride or the like, affords a mixture of the 4-chloro (6) and 6-chloro (7) derivatives, which function as intermediates to other pyridine ring substituted analogs via nucleophilic displacement reactions and the like. Representative compounds of the 7-aza subclass are listed in Table I.

TABLE I
2-ARYL-7-AZA-BENZO[b]THIOPHENES

| $X_2$ | R | m.p. |
|---|---|---|
| H | H | 234–235° |
| 3-OCH$_3$ | H | 187–189° |
| 4-OCH$_3$ | H | 209–212° |
| 4-OCH$_3$ | COCH$_3$ | 140–141° |
| 2-OCH$_3$ | H | 142–144° |
| H | COCH$_3$ | 86–87.5° |
| 4-CF$_3$ | H | 261–264° |
| 4-F | COCH$_3$ | 152–154° |
| 4-CF$_3$ | COCH$_3$ | 133–134° |
| H | COCH$_2$OCH$_3$ | 88–91° |

| R | m.p. |
|---|---|
| H | 245–248° (d) |
| Ac | 115–116° |

| R | m.p. |
|---|---|
| CH$_2$OMe | 54° |
| H | 181–183° |
| Ac | 128–129° |

II. 2-Aryl-6-Azabenzo [b]thiophenes

As shown below in scheme (e), compounds of this subclass are prepared by treatment of a 3-halo-4-cyanopyridine (8) with the appropriately substituted arylmethylmercaptide, which was obtained by treatment of the mercaptan with a base, such as sodium methoxide, sodium hydride, triethylamine, lithium diisopropylamide, etc., in a solvent such as acetonitrile, N,N-dimethylformamide, dimethyl-sulfoxide, tetrahydrofuran at temperatures from −78° C. to 65° C. for 30 minutes to 24 hours. The derived 3-arylmethylthio-4-cyanopyridines are saponified to the corresponding acids with base, such as aqueous sodium hydroxide or potassium hydroxide, followed by acidification. The acids are esterified either by treatment with carbonyldiimidazole in tetrahydrofuran or dimethylformamide for 1–6 hours at 0°–65° C. followed by treatment with methanol for 1–6 hours at room temperature or by heating with methanol, dimethoxypropane, and sulfuric acid under reflux for 12–36 hours. The derived methyl-3-arylmethylthiopyridine4-carboxylates (11) are ring-closed to the 2-aryl-3-hydroxy-6-azabenzo[b]thiophenes (12) and further modified as described for the 7-aza series.

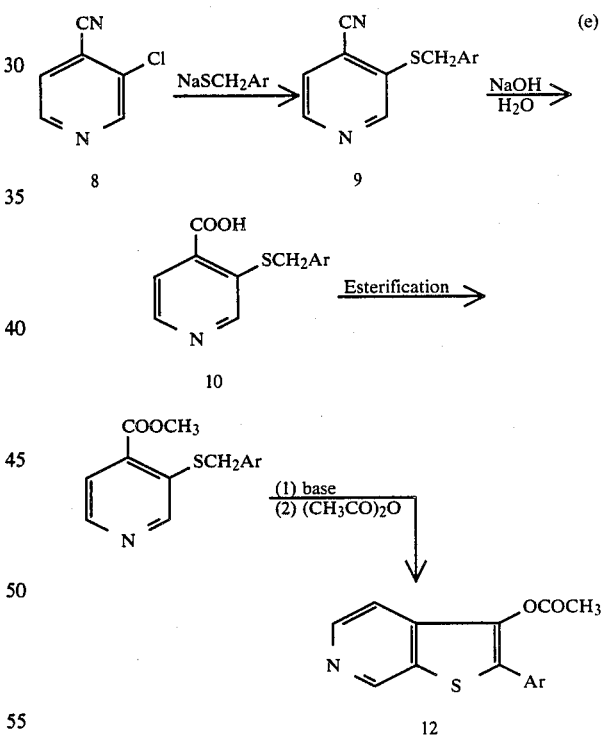

Alternatively, as shown below in scheme (f), the 6-aza series may be derivatized selectively at the 7-position by lithiation with n-butyllithium-TMEDA complex to generate the 7-lithio species, which then can be reacted with an electrophile such as benzaldehyde.

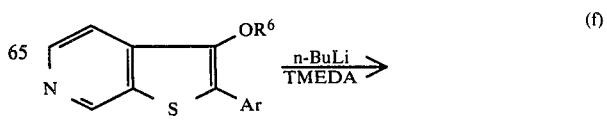

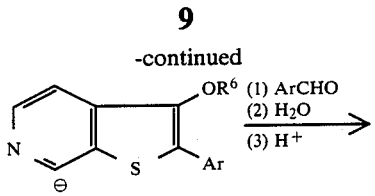

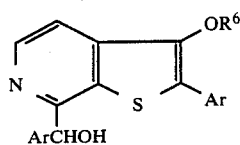

III. 2-ARYL-5-AZA-BENZO[b]THIOPHENES

Compounds of this subclass are prepared in an analogous fashion as that described for the 7-aza series, but employing as starting material 4-mercaptonicotinic acid obtained by the process set forth in L. Katz, M. S. Cohen, and W. Schroeder, U.S. Pat. No. 2,824,876 (2-2-5-58).

Alternatively, the 5-aza-benzo[b]thiophenes can be prepared from 4-chloronicotinic acid by the process set forth in W. C. J. Ross, *J. Chem. Soc.* (C), 1816 (1966). Displacement of the chloro group by an appropriately substituted arylmethyl mercaptide is carried out in a solvent such as N,N-dimethylformamide, dimethylsulfoxide, tetrahydrofuran, or the like, at a temperature of from 0° to 65° C. for a period of from 30 minutes to 24 hours. The derived 4-aryl-methylthionicotinic acids are then esterified, ring closed and further modified as described for the 7-aza series to the desired 2-aryl-3-hydroxy-5-aza-benzo[b]thiophenes (9).

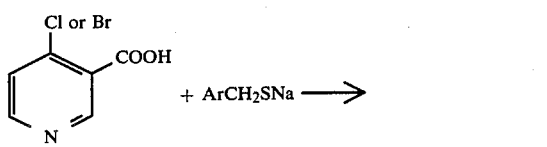

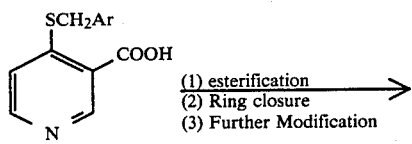

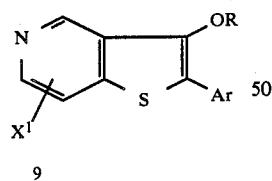

9

IV. 2-Aryl-4-Azabenzo[b]thiophenes

As illustrated by the following scheme (h), compounds of this subclass are prepared from available methyl 3-hydroxypyridine-2-carboxylates (13). The 3-hydroxy compounds are converted to the 3-mercaptans by treatment of (13) with N,N-dimethyl-aminothiocarbamoyl chloride and a base, such as sodium or potassium hydroxide, in aqueous tetrahydrofuran or dioxane for 1-6 hours at room temperature. The resulting thiocarbamates are isomerized by heating at temperatures between 160°-240° C. in a solvent such as o-dichlorobenzene or m-dimethoxybenzene for 1-8 hours. The N,N-dimethylaminocarbamoyl mercaptans are deblocked by treatment with sodium methoxide-methanol at room temperature for 10-60 minutes and the resulting mercaptides are alkylated with an arylmethylchloride in a solvent such as tetrahydrofuran, N,N-dimethylformamide, or dioxane at room temperature for 1-24 hours. Ring closure is effected by treatment with base, such as lithium diisopropylamide in tetrahydrofuran at 78° C. or by the methods described for the 7-aza series.

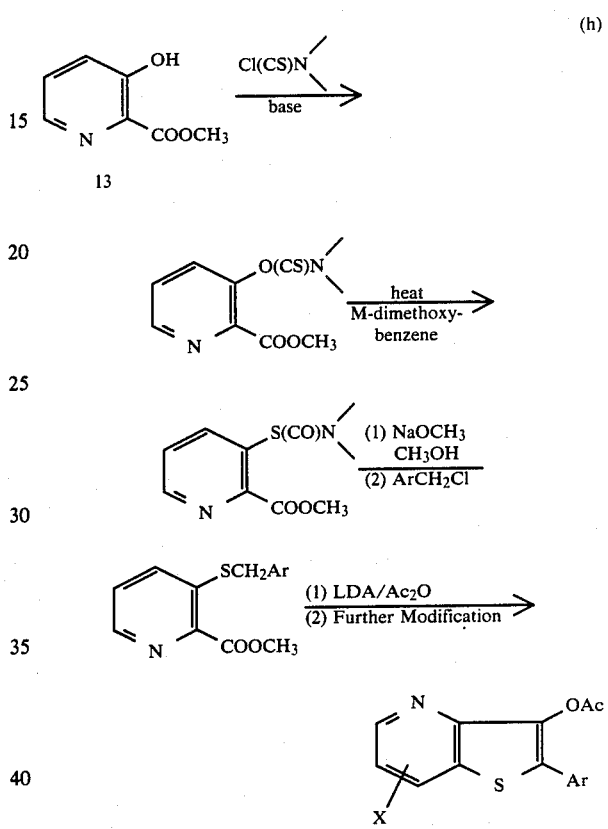

The following examples illustrate but do not limit the present invention.

EXAMPLE 1

Preparation of 7-aza-3-hydroxy-2-(3-methoxyphenyl)benzo[b]thiophene

Step A: Preparation of 2-(3-Methoxybenzylthio)-nicotinic acid

A suspension of 4.65 g (0.03 mole) of 2-mercaptonicotinic acid in 100 ml of methanol was cooled in ice as 3.24 g (0.06 mole) of sodium methoxide was added. The resulting solution was left at ice-temperature as 4.68 g (0.03 mole) of 3-methoxybenzyl chloride was added over 5 minutes. The reaction mixture was stirred for 14 hours and the reaction set solid. The addition of 50 ml of water caused solution and an excess of acetic acid precipitated 7.55 g (92% of theory) of 2-(3-methoxybenzylthio)nicotinic acid. Recrystallization was effected from ethyl acetate; m.p. 156-157° C.

Anal.: Calc'd. for $C_{14}H_{13}NO_3S$. C=61.09; H=4.76, N=5.09. Found: C=61.19, H=4.83, N=5.22.

Step B: Preparation of Methyl 2-(3-methoxy benzylthio)nicotinate

A suspension of 7.15 g (0.026 mole) of 2-(3-methoxybenzylthio)nicotinic acid in 75 ml of dry acetonitrile was treated with 3.95 g (0.026 mole) of 1,8-diazabicyclo[5,4,0]-under-7-ene (DBU). A solution formed and 4.26 g (0.030 mole) of methyl iodide was added over one minute. After keeping the reaction mixture at room temperature for 24 hours, the solution was evaporated in vacuo. The residue was partitioned between 100 ml of ether and 50 ml of water. The ether layer was washed with 50 ml of $H_2O$, dried, and evaporated to a small volume. The addition of hexane with cooling yielded 6.9 g (92% of theory) of methyl 2-(3-methoxybenzylthio)nicotinate; m.p. 69°–70° C.

Anal.: Calc'd. for $C_{15}H_{15}NO_3S$.
C=62.28, H=5.23, N=4.84. Found: C=62.09, H=5.28, N=4.83.

Step C: Preparation of 7-Aza-3-hydroxy-2-(3-methoxy phenyl)-benzo[b]thiophene To a stirred solution of 5.78 g (0.02 mole) of methyl 2-(3-methoxybenzylthio)nicotinate in 30 ml of dry N-methylpyrrolidinone was added 800 mg (0.02 mole) of 60% sodium hydride dispersion. The reaction was stirred at room temperature for 14 hours then poured into ice water. The solution was extracted with 50 ml of hexane, and the aqueous layer was treated with an excess of acetic acid to precipitate 7-aza-3-hydroxy-2-(3-methoxyphenyl)benzo[b]thiophene; yield 4.4 g (86% of theory). The crude product was recrystallized from ethyl acetate; m.p. 187°–189° C. Anal.: Calc'd. for $C_{14}H_{11}NO_2S$. C=65.37, H=4.31, N=5.44. Found: C=65.31, H=4.35, N=5.40.

EXAMPLE 2
3-Acetoxy-6-(1,1-dimethylethyl)-2-phenyl-7-azabenzo[b]- thiophene

Step A: Preparation of 2-Phenylmethylthionicotinic acid

A sample of 15.5 g (100 mmol) of 2-mercaptonicotinic acid was dissolved in 50 mL of 4.1M sodium methoxide in methanol and 100 mL of methanol. To this was added 18.8 g (110 mmol) of benzyl bromide and the solution was stirred at room temperature for 3 hours. Then 250 mL of water was added and the solution was acidified to pH 7 with glacial acetic acid. The precipitate was collected, washed with water, and dried to afford 22.3 g (91%) of white solid.

Step B: Preparation of Methyl 2-phenylmethylthionicotinate

A solution of 18.3 g (75 mmol) of 2-phenylmethylthionicotinic acid and 16.2 g (100 mmol) of carbonyldiimidazole in 250 mL of dry dimethylformamide was stirred at room temperature for 2 hours. The solution was cooled to 0° and 25 mL of 4M sodium methoxide in methanol was added. After warming to room temperature the solution was partitioned between ether and water and the aqueous layer was washed with two portions of ether. The ether extracts were washed with brine, dried over $MgSO_4$, and concentrated. The residue was crystallized from ether-hexane to afford 17.4 g (89%) of fine white needles, which was used in the next step without further purification.

Step C: Preparation of 3-Hydroxy-2-phenyl-7-azabenzo[b]thiophene

A suspension of 12.9 g (50 mmol) of methyl 2-phenylmethylthionicotinate and 2.6 g (110 mmol) of sodium hydride in 100 mL of dry N,N-dimethylformamide was stirred for 4 hours at room temperature. The solution was diluted with 200 mL water and acidified with glacial acetic acid. The precipitate was collected, washed with water, and dried to afford 10.6 g (93%) of a white crystalline solid to be used in the next step.

Step D: Preparation of 3-Methoxymethoxy-2-phenyl-7-azabenzothiophene

A suspension of 4.54 g (20 mmol) of 3-hydroxy-2-phenyl-7-azabenzo[b]thiophene and 2.75 g (22 mmol) of potassium t-butoxide in 50 mL of tetrahydrofuran was stirred until the solid dissolved. Then 2.0 g (25 mmol) of chloromethyl methyl ether was added and the solution was stirred at room temperature for 2 hours. The solution was partitioned between ether and water and the aqueous layer was washed with two portions of ether. The ether extracts were washed with brine, dried over $MgSO_4$, and concentrated to 4.33 g (80%) of an oil that crystallized upon standing, m.p. 54° C.

Step E: Preparation of 6-(1,1-dimethylethyl)-3-hydroxy-2-phenyl-7-azabenzo[b]thiophene A solution of 2.72 g (10.0 mmol) of 3-methoxymethoxy-2-phenyl-7-azabenzothiophene in 20 mL of dry tetrahydrofuran was cooled to −78° C. To this was added 11 mL of a 1.0M solution of t-butyllithium in hexane and the solution was allowed to warm to room temperature. The solution was quenched with methanol and stirred in air for 60 minutes, then partitioned between ether and water. The aqueous layer was washed with two portions of ether and the combined extracts were washed with brine, dried, and concentrated to an oil. The oil was dissolved in 10 mL methanol and 10 mL of 2M HCl and stirred at room temperature for 24 hours. The solution was partitioned between ether and water and the ether layer dried and concentrated. Recrystallization from ether-hexane afforded 2.43 g (84%) of pale yellow needles, m.p. 181°–183° C.

Step F: Preparation of 3-Acetoxy-6-(1,1-dimethylethyl)-2-phenyl-7-azabenzo[b]thiophene A solution of 1.42 g (5 mmol) of 6(1,1-dimethylethyl)-3-hydroxy-2-phenyl-7-azabenzo[b]thiophene and 1.42 g sodium acetate in 20 mL of acetic anhydride was heated at reflux for 1 hour. The solution was concentrated and the residue was partitioned between ether and water. The ether layer was washed with sodium bicarbonate solution and brine, dried and concentrated. The residue was crystallized from ether-hexane to afford 1.49 g (91%) of fine white needles, m.p. 128°–9° C.

EXAMPLE 3
3-Hydroxy-2-(4-methoxyphenyl)-6-azabenzo[b]thiophene

Step A: Preparation of 4-Cyano-3-(4-methoxyphenyl)methylmercaptopyridine

A solution of 6.2 g (40 mmol) of p-methoxybenzylmercaptan in 9.8 mL of 4.4M sodium methoxide in methanol was added dropwise to a solution of 5.52 g (40 mmol) of 3-chloro-4-cyanopyridine in dry acetonitrile that has been cooled in an ice bath. After addition was complete the solution was allowed to warm to room temperature over 2 hours. The solvent was concentrated and the residue was partitioned between dichloromethane and water. The aqueous layer was extracted with two portions of dichloromethane and the combined extracts were washed with brine, dried (MgSO4) and concentrated to afford 6.1 g (60%) of a pale yellow crystalline solid, m.p. 80°–81° C.

Step B: Preparation of 3-(4-methoxyphenyl)methylthiopyridine-4-carboxylic acid A solution of 6.0 g (23.4 mmol) of 4-cyano-3-(methoxyphenyl)methylthiopyridine in 15 mL of 6M NaOH was heated under reflux for 6 hours. The solution was cooled, and acidified with glacial acetic acid. The precipitate was collected by filtration and triturated with two portions of cold ether to afford 6.0 g (94%) of white crystals, m.p. 250° C. (decomp.).

Step C: Preparation of Methyl 3-(4-methoxyphenyl)methylthiopyridine-4-carboxylate A solution of 4.9 g (17.8 mmol) of 3-(4-methoxyphenyl)methylthiopyridine-4-carboxylic acid and 4.9 g (30 mmol) of carbonyldiimidazole in 50 mL of dry N,N-dimethylformamide was stirred at 0° C. for 10 minutes and then allowed to warm to room temperature. After 2 hours the solution was cooled to 10° C. and quenched with 20 mL of methanol. The mixture was stirred for 2 hours and then the solvent was concentrated. The residue was partitioned between ether and water and the aqueous layer was extracted with three portions of ether. The ether extracts were dried (MgSO4) and concentrated to afford 5.1 g (93%) of a crystalline solid, m.p. 99°–100° C.

Step D: Preparation of 3-Acetoxy-2-(4-methoxyphenyl)-6-azabenzo[b]thiophene

A solution of 0.200 g (.69 mmol) of methyl 3-(4-methoxyphenyl)methylthiopyridine-4-carboxylate in 2 mL of dry tetrahydrofuran was added to a suspension of 83 mg (2.1 mmol) of 60% dispersion of sodium hydride in 2 mL of dry N,N-dimethylformamide. The mixture was stirred at room temperature for 3 hours, then poured onto ice water and acidified with glacial acetic acid. The solid material (product) was collected by filtration and the filtrate was extracted with ethyl acetate. The ethyl acetate extract was dried, concentrated and combined with the solid precipitate that had been collected. This material was heated at reflux with 100 mg sodium acetate in 2 mL of acetic anhydride for 2 hours, then was partitioned between ethyl acetate and water. The aqueous layer was washed with two portions of ethyl acetate and the combined extracts were dried and concentrated. The residue was crystallized from methanol to afford 100 mg (48%) of white crystalline material, m.p. 141–142° C.

EXAMPLE 4

3-Acetoxy-2-phenyl-6-azabenzo[b]thiophene

Step A: Preparation of 4-Cyano-3-phenyl-methylthiopyridine

Prepared from 4.3 g (31.1 mmol) of 3-chloro--4-cyanopyridine as in example, Step A., except that benzylmercaptan was used instead of p-methoxybenzylmercaptan to afford 6.1 g (87%) of a pale unstable oil that was used directly in step B.

Step B: Preparation of 3-Phenylmethylthiopyridine-4-carboxylic acid

Prepared from 6.1 g of material from Step A by the procedure described in example, Step B to afford 5.7 g (86%) of white crystalline material, m.p. 240°–5° C., (decomp.).

Step C: Preparation of Methyl 3-phenylmethylthiopyridine-4-carboxylate

A solution of 5.1 g (20 mmol) of 3-phenylmethylthiopyridine-4-carboxylic acid in 150 mL of methanol, 1.6 mL of 2,2-dimethoxypropane, and 5 mL of sulfuric acid was heated at reflux for 18 hours. The solution was cooled, concentrated to 25 mL, then partitioned between ether and sodium bicarbonate solution. The ether layer was washed with sodium bicarbonate solution, then brine, then dried and concentrated to afford 5.0 g (96%) of white crystals, m.p. 79°–80° C.

Step D: Preparation of 3-Hydroxy-2-phenyl-6-azabenzo[b]thiophene

A solution of 4.8 g (19 mmol) of methyl 3-phenylmethylthiopyridine-4-carboxylate in 10 mL of tetrahydrofuran was added to a slurry of 2.40 g (60 mmol) of 60% sodium hydride in 10 mL of N,N-dimethylformamide and the resulting mixture was stirred at 60° C. for 3 hours. The solution was poured onto ice water and acidified with glacial acetic acid. The filtrate was collected to afford 1.6 g (38%) of white solid.

Step E: Preparation of 3-Methoxymethoxy-2-phenyl-6-azabenzo[b]thiophene

A solution of 1.1 g (4.8 mmol) 3-hydroxy-2-phenyl-6-azabenzo[b]thiophene and 0.116 g (4.8 mmol) of sodium hydride in 15 mL of tetrahydrofuran was stirred at room temperature for 15 minutes. Then 0.37 mL (5.0 mmol) of chloromethyl methyl ether was added and the solution was stirred at room temperature for 2 hours. The solution was partitioned between ether and water and the ether extract was concentrated to afford 1.2 g (92%) of white crystalline material, m.p. 55–56° C.

Step F: Preparation of 7-(Hydroxyphenylmethyl)-3-methoxymethoxy-2-phenyl-6-azabenzo[b]thiophene A solution of 0.43 g (3.7 mmol) of N,N,N',N'-tetramethylethylenediamine and 1.8 mL of 2.6M n-butyllithium was stirred at −20° for 1 hour, then cooled to −60°.

A solution of 1.0 g (3.7 mmol) of 3-methoxymethoxy-2-phenyl-6-azabenzo[b]thiophene in 5 mL of dry ether was added and the solution was kept at −60° for 3 hours. The reaction was quenched with 0.5 mL of benzaldehyde and allowed to warm to room temperature. The mixture was partitioned between ether and water and the aqueous layer was washed with ether. The combined extracts were dried and concentrated to an oil. Chromatography on silica gel (30% ethyl acetate-hexane) afforded 0.62 g (44%) of a colorless oil, NMR (200 MHz, CDCl3) δ3.4 (s, 3H), 5.0 (s, 2H), 5.95 (s, 1H, —OH), 7.2-7.8-(m, 12H), 8.52 (d, J=6Hz, 1H), Mass Spec m/e 377 (M+).

Step G: Preparation of 7-(Hydroxyphenylmethyl)-3-hydroxy-2-phenyl-6-azabenzo[b]thiophene A solution of 0.61 g (1.8 mmol) of 7-(hydroxyphenylmethyl)-3-methoxymethyl-2-phenyl-6-azabenzo[b]thiophene in 2.7 mL of 2M HCl and 2.7 mL of methanol was heated at reflux for 30 minutes. The solution was cooled and partitioned between ethyl acetate and water. The ethyl acetate layer was dried and concentrated to afford 0.50 g (93%) of white solid, m.p. 214°–215° C.

EXAMPLE 5

5-Aza-3-hydroxy-2-phenylbenzo[b]thiophene

Step A: Preparation of 4-Benzylthionicotinic acid

To a stirred suspension of 1.55 g (0.01 mole) of 4-mercaptonicotinic acid (prepared by the process set forth in L. Katz, M. S. Cohen, and W. Schroeder, U.S. Pat. No. 2,824,876) in 20 mL of dry methanol cooled in ice and stirred, was added 1.08 g (0.02 mole) of sodium methoxide. The yellow solution was cooled in ice and 1.71 g (0.01 mole) of benzyl bromide was added. Within one hour there was a new solid formation with loss of the yellow color. The reaction was kept for 2 more hours at room temperature, then most of the solvent was removed in vacuo. The solid residue was taken up in 50 mL of water and acidified with an excess of acetic acid to precipitate 2.45 g (100% of theory) of 4-(benzylthio) nicotinic acid which melted at 232°–234° C.

Step B: Preparation of Methyl 4-benzylthionicotinate

A suspension of 2.45 g (0.01 mole) of 4-benzylthionicotinic acid in 35 mL of dry acetonitrile was treated with 1.52 g (0.01 mole) of 1,8-diazabicyclo[5,4,0]undec-7-ene (DBU). 1.7 g (0.01 mole) of methyl iodide was added and stirring was continued for 7 hours. The reaction was carefully diluted with water to crystallize 430 mg of methyl 4-benzylthionicotinate which melted at 98°–99° C.

Anal.: Calc'd. $C_{14}H_{13}NO_2S$. C=64.86, H=5.05, N=5.40. Found: C=65.11, H=5.28, N=5.65.

Step C: Preparation of 5-Aza-3-hydroxy-2-phenylbenzo[b]thiophene

A solution of 3.36 g (0.03 mole) of potassium tert-butoxide in 90 mL of dry tetrahydrofuran was cooled to ice-temperature and stirred as 2.59 g (0.01 mole) of methyl 4-benzylthionicotinate was added. The yellow-orange solution was stirred at ice-temperature for 15 minutes, then at room temperature overnight. Most of the tetrahydrofuran was evaporated in vacuo. The residue was taken up in 100 mL of ice water and heated with an excess of acetic acid to obtain 1.91 g (84% of theory) of 5-aza-3-hydroxy-2-phenylbenzo[b]thiophene, which was recrystallized from N,N-dimethylformamide-ether giving a melting point of 260° C.

Anal.: Calc'd. for $C_{13}H_9NOS$. C=68.72, H=3.99, N=6.16. Found: C=68.34, H=4.09, N=6.18.

EXAMPLE 6

3-Acetyloxy-5-aza-2-phenylbenzo[b]thiophene

A mixture of 200 mg of 5-aza-3-hydroxy-2-phenylbenzo[b]thiophene, 10 mg of p-toluenesulfonic acid, and 2 mL of acetic anhydride was heated on a steam bath for three hours, then evaporated in vacuo. The residue was taken up in 15 mL of ethyl acetate and 15 mL of ether, washed with 10 mL of 1% sodium bicarbonate solution, dried, concentrated to a small volume, and finally diluted with hexane to crystallize 155 mg (65% of theory) of 3-acetyloxy-5-aza-2-phenylbenzo[b]thiophene; m.p. 101°–103° C.

Anal.: Calc'd. for $C_{15}H_{11}NO_2S$. C=66.91, H=4.12, N=5.20. Found: C=66.96, H=4.19, N=5.53.

EXAMPLE 7

5-Aza-3-hydroxy-2-(4-methoxyphenyl)-benzo[b]thiophene

Step A: Preparation of 4-(4-methoxybenzylthio)-nicotinic acid

A stirred and ice-cooled mixture of 788 mg (0.005 mole) 4-chloronicotinic acid [prepared by the process set forth in W. C. J. Ross, *J. Chem. Soc.*(C), 1816 (1966)] and 771 mg (0.005 mole) of 4-methoxybenzylmercaptan in 6 mL of dry N,N-dimethylformamide was treated with 480 mg (0.012 mole) of 60% sodium hydride dispersion. The reaction was stirred at room temperature for 4 hours during which a thick solid formed, which was taken up in 75 mL of ice water. After extraction with 25 mL of hexane, the aqueous layer was acidified with 2.5N hydrochloric acid to precipitate 4-(4-methoxybenzylthio)-nicotinic acid; yield 1.2 g (89% of theory), m.p. 230° C.

Step B: Preparation of Methyl 4-(4-methoxybenzylthio)nicotinate

A suspension of 2.2 g (0.008 mole) of 4-(4-methoxybenzylthio)-nicotinic acid in 30 mL of dry N,N-dimethylformamide was reacted with 1.78 g (0.011 mole) of 1,1'-carbonyldiimidazole. This was stirred at room temperature for 2 hours, then 0.5 mL of 4.3M sodium methoxide in methanol and 5 mL of methanol. The reaction was stirred for 1 hour at room temperature, then partitioned between 75 mL of ether and 30 mL of water. The ether layer was extracted with 2×30 mL of water, dried, concentrated to a small volume, and hexane added to crystallize methyl 4-(4-methoxybenzylthio) nicotinate; yield 1.66 g (72% of theory), m.p. 108°–110° C.

Anal.: Calc'd. for $C_{15}H_{15}NO_3S$. C=62.28, H=5.23, N=4.84. Found: C=62.41, H=5.41, N=4.69.

Step C: Preparation of 5-Aza-3-hydroxy-2-(4-methoxyphenyl)benzo[b]thiophene

A solution of 672 mg (0.006 mole) of potassium tert-butoxide in 10 mL of dry tetrahydrofuran was stirred at ice-temperature while 579 mg (0.002 mole) of methyl 4-(4-methoxybenzylthio) nicotinate was added over 3 minutes. The yellow solution was stirred for 10 more minutes at ice-temperature, then at room temperature for 2½ hours. The reaction was diluted with 50 mL of ethyl acetate, and 0.5 mL of acetic acid was added. This was extracted with 3×30 mL of H₂O. The organic layer was dried and evaporated leaving 230 mg (45% of theory) of 5-aza-3-hydroxy-2-(4-methoxyphenyl)-benzo[b]thiophene. Recrystallization was effected from tetrahydrofuran, m.p. 222°–225° C.

Anal.: Calc'd. for $C_{14}H_{11}NO_2S$. C=65.37, H=4.31, N=5.44. Found: C=65.09, H=4.50, N=5.29.

5-Aza-3-hydroxy-2-(4-methoxyphenyl)benzo[b]thiophene can also be prepared by dissolving methyl 4-(4-methoxybenzylthio)nicotinate in 8 mL of dry N,N-dimethylformamide. This was stirred and cooled in ice as 120 mg (0.005 mole) of NaH was added. After reaction was stirred at room temperature overnight, it was diluted with 100 mL of ice water and decolorized with charcoal. An excess of acetic acid precipitated 5-aza-3-hydroxy-2-(4-methoxyphenyl)benzo-[b]thiophene; yield 575 mg (75% of theory), m.p. 223°–225° C.

EXAMPLE 8

3-Acetyloxy-5-aza-2-(4-methoxyphenyl)benzo[b]thiophene

A mixture of 500 mg of 5-aza-3-hydroxy-2-(4-methoxyphenyl)benzo[b]thiophene, 20 mg of p-toluenesulfonic acid, and 8 mL of acetic anhydride was heated on a steam bath for 3 hours, then evaporated. The crystalline residue was triturated with water, then recrystallized from methylene chloride-hexane to give 360 mg (62% of theory) of 3-acetyloxy-5-aza-2-(4-methoxyphenyl)-benzo[b]thiophene, m.p. 125°–127° C.

Anal.: Calc'd. for $C_{16}H_{13}NO_3S$. C=64.21, H=4.38, N=4.68. Found: C=64.56, H=4.19, N=4.43.

EXAMPLE 9

3-Acetyloxy-2-(4-methoxyphenyl)-4-azabenzo[b]thiophene

Step A: Preparation of Methyl 3-(N,N-dimethylaminothiocarbamoyloxy)pyridine-2-carboxylate A solution of 3.06 g (20 mmol) of methyl 3-hydroxypyridine-2-carboxylate in 15 mL of water was made basic with 1.12 g KOH. To this solution was added 3.2 g (26 mmol) of N,N-dimethylaminothiocarbamoyl chloride and the solution was stirred at room temperature for 2 hours. The solution was partitioned between benzene and water and the aqueous layer was washed with two portions of water. The combined extracts were dried and concentrated to afford 4.1 g of a white solid, m.p. 74°–75° C.

Step B: Preparation of Methyl 3-(N,N-dimethylaminocarbamoylthio)pyridine-2-carboxylate A solution of 2.9 g (12.1 mmol) of methyl 3-(N,N-dimethylaminothiocarbamoyloxy)pyridine-2-carboxylate in 10 mL of m-dimethoxybenzene was heated to 230° for 2 hours. The solution was cooled and filtered through silica with hexane to remove the m-dimethoxybenzene. Then the silica was washed with acetone to afford 2.4 g (83%) of a pale tan solid, m.p. 56°–58° C.

Step C: Preparation of Methyl 3-(4-methoxyphenylmethylthio)pyridine-2-carboxylate A solution of 1.20 g (5 mmol) of methyl 3-(N,N-dimethylaminocarbamoylthio)pyridine-2-carboxylate in 5 mL of methanol and 1.5 mL (6 mmol) of 4.1M sodium methoxide methanol was stirred at room temperature for 10 minutes. Then the solvent was concentrated and the residue was dissolved in 5 mL of N,N-dimethylformamide and 5 mL of tetrahydrofuran. 0.936 g (6 mmol) of p-methoxybenzylmercaptan was added and the solution was stirred at room temperature for 18 hours. The solution was partitioned between ether and water and the aqueous layer was extracted with two portions of ether. The combined extracts were washed with brine, dried and concentrated. Recrystallization from methanol afforded 0.90 g (62%) of pale tan needles, m.p. 99°–100° C.

Step D: Preparation of 3-Acetyloxy-2-(4-methoxyphenyl)-4-azabenzo[b]thiophene A solution of 0.65 g (2.24 mmol) of methyl 3-(4-methoxyphenylmethylthio)pyridine-2-carboxylate in 5 mL of dry tetrahydrofuran was added to a solution of 2.6 mmol of lithium diisopropylamide in dry tetrahydrofuran at −78° C. After 30 minutes the solution was partitioned between ether and water and the aqueous layer was saturated with NaCl and washed with two portions of dichloromethane. The combined extracts were dried and concentrated to an oil that was dissolved in 2 mL of acetic anhydride and 200 mg of sodium acetate. This solution was heated at reflux for 1 hour, then partitioned between ether and water. The aqueous layer was washed with two portions of ether and the combined extracts concentrated. The residue was chromatographed on HPLC (silica, 30% ethyl acetate-hexane) to afford 101 mg (15%) of white crystals, m.p. 146°–148° C.

C. Utility of the compounds within the scope of the invention

This invention also relates to a method of treatment for patients (or mammalian animals raised in the dairy, meat, or fur industries or as pets) suffering from disorders or diseases mediated by the inhibition of the oxidation of arachiodonic acid and/or leukotrienes, and gastric irritation or lesion. More specifically, this invention is directed to a method of treatment involving the administration of one or more of the enzyme inhibitors of formula (I) as the active constituent.

Accordingly, a compound of Formula (I) can be used among other things to reduce pain and inflammatory conditions, including rheumatoid arthritis, osteoarthritis, gout, psoriasis, inflammatory bowel disease and inflammation in the eye that may be caused by ocular hypertension and may eventually lead to glaucoma. It can also be used to correct respiratory, cardiovascular, and intravascular alterations or disorders, and to regulate immediate hypersensitivity reactions that cause human asthma and allergic conditions.

For the treatment of inflammation, arthritis conditions, cardiovascular disorder, allergy, psoriasis, asthma, or other diseases mediated by prostaglandins and/or leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
(1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3)esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of formula (I) may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 2.5 to about 75 mg of the compound per kilogram of body weight per day (about 75 mg to about 3.75 gms per patient per day).

D. Biological Data Supporting the Utility of the Compounds Within the Scope of the Invention.

The following is a summary of biological data from two bioassays. These data serve to illustrate that the compound of formula (I), for example, 7-aza-3-acetyloxy-2-phenyl-benzo[b]thiophene (compound A) and 7-aza-3-acetyloxy-2-(4-fluorophenyl)-benzo[b]thiophene, (compound B) are useful in the treatment of leukotriene mediated diseases.

1. Brewer's Yeast Hyperalgesia Assay*

*Winter, C. A. et al., J. Pharm. Exp. Ther. 150, 165–171 (1965).

In this assay, which is sensitive to inhibition by lipoxygenase and cyclooxygenase inhibitors, compounds of formula I reduced the pain response induced by Brewer's yeast (Table 1a).

Groups of 10 female Sprague-Dawley rats, weighing 35–50 grams (Charles River Breeding Laboratories), were fasted overnight prior to testing. For each animal, 0.1 ml of the edema-inducing Brewer's yeast suspension (5% homogenate in physiological saline) was injected into the right hindpaw. Pain threshold was measured by applying pressure to the plantar surface of the hindpaw by means of a compressed air driven piston with a 2 mm. tip. Testing was carried out 3, 4, and 5 hours after the yeast injection. Compounds, prepared as homogenates in either 1% methylcellulose or aqueous vehicle, were administered orally 60 minutes before testing. A group of vehicle treated control animals was included in each experiment. Squeak pressure thresholds were measured and recorded for the compound and vehicle-treated groups of rats 3, 4, and 5 hours after administration of the Brewer's yeast (60 minutes after compound treatment). The estimation of analgesia was as follows: 1. the mean response pressure for the daily vehicle control group in the normal and inflamed foot was calculated; 2. for each compound treatment group, the number of animals with response pressures equal to or greater than 25 mm Hg was noted. These animals were considered to be analgesic.

Following is data obtained using these various assays with representative compounds of Formula I.

TABLE 1a

Effect of Compounds of Formula (I) on Yeast Hyperalgesia in the Rat

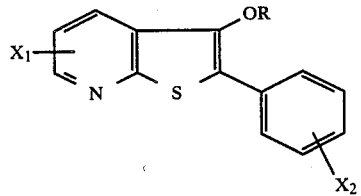

| R | $X^1$ | $X^2$ | Dose (mg/kg p.o.) | % Inhibition |
|---|---|---|---|---|
| (CO)CH$_3$ | H | H | 3 | 60 |
| (CO)CH$_3$ | H | p-OCH$_3$ | 3 | 10 |
| H | H | p-OCH$_3$ | 3 | 60 |
| (CO)CH$_3$ | H | p-F | 3 | 70 |
| (CO)CH$_2$OCH$_3$ | H | H | 3 | 50 |
| (CO)CH$_3$ | 6-Cl | H | 3 | 40 |
| (CO)CH$_3$ | 6-OCH$_3$ | H | 3 | 60 |
| (CO)CH$_3$ | 7-OCH$_3$ | H | 3 | 50 |
| (CO)CH$_3$ | 7-CN | H | 3 | 60 |
| H | 7-CN | H | 3 | 50 |

2. Inhibition of PMN 5-lipoxygenase in the rat Methods:

PMN Isolation:

Male Sprague-Dawley rates under ether anesthesia were injected i.p. with 8 mls of 12% aqueous sodium caseinate. After 15–24 hours the animals were sacrificed with CO$_2$ and the peritoneal cavities were lavaged with Eagles MEM with Earles salts and containing L-glutamine and 30 mM HEPES. The pH was adjusted to 7.4. The lavage fluid was centrifuged for 5 minutes at 350×g at room temperature. The cells were resuspended in fresh medium and filtered through lens paper. The cells were pelleted again and reconstituted to a concentration of 1×10$^7$ cells/ml with fresh medium.

Incubations:

The experiments were run as follows: 0.5μ of test compound in DMSO or 0.5 μl DMSO alone was added to reaction tubes. 0.5 ml aliquots of the stirred PMN suspension maintained at 37° C. were then added. After 2 minutes, 0.5 μl of 10 mM A23187 (final concentration=10 μM) or 5 μl of DMSO was added and allowed to incubate for 4 additional minutes at 37° C. The reaction was stopped by the addition of 0.5 ml of cold methanol. The precipitated proteins were removed by centrifugation and the supernatant fluid was analyzed via RIA or HPLC.

Radioimmunoassay determinations of LTB$_4$

Radioimmunoassays were performed using the dextran-coated charcoal binding method as described by J. L. Humes in Methods for Studying Mononuclear Phagocytes (Eds. D. Adams et al.) p. 641, Academic Press, N.Y. (1981).

Aliquots, 2 μl, of the supernatant fluids were added to assay tubes and incubated for 10 minutes at 37° C. to remove methanol. Fifty μl of tissue culture medium M-199 containing 1 percent heat-inactivated-porcine serum was then added to each tube. Standard amounts of LTB$_4$ were also prepared in this medium so that 50 μl aliquots contained 25–1000 pg. Antisera to LTB$_4$ was diluted 1:3000 with 10 mM potassium phosphate, pH 7.3 containing 1 mM ethylenediaminetetracetic acid and 0.25 mM thimerasol (PET buffer). Aliquots, 100 μl, of the diluted antisera were added to both standard and unknown tubes and incubated at room temperature for 0.5 hour. (5,6,8,9,11,12,14,15-$^3$H)-LTB$_4$ (Amersham, 150 Ci/mMol) was diluted with PET to a concentration of 1 nCi/ml. Aliquots, 100 μl were added and the mixture incubated for 2 hours at room temperature or alternatively overnight at 4° C. One ml of dextran-coated charcoal solution is added to all tubes. After centrifugation for 10 minutes at 1000×g the radioactivity in the supernatant fluid was determined.

The dextran-coated charcoal removes the unbound $^3$H-LTB$_4$. Therefore in this procedure the antibody-bound-$^3$H-LTB$_4$ is measured. The RIA[4] determinations are performed on single samples.

TABLE 3

Effect of Compounds of formula (I) on PMN-5-lipoxygenase

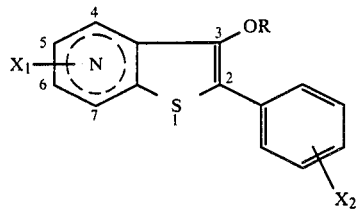

| Position of N | R | X₁ | X₂ | Dose mg/ml | % Inhibition |
|---|---|---|---|---|---|
| 5 | (CO)CH₃ | 4-CH₃, 6-CH₃ | p-OCH₃ | 0.3 | 75 |
|  |  |  |  | 0.1 | 45 |
|  |  |  |  | 0.03 | 4 |
| 7 | (CO)CH₃ | H | p-CF₃ | 1 | 100 |
|  |  |  |  | 0.3 | 100 |
|  |  |  |  | 0.1 | 61 |
| 7 | " | H | p-F | 0.1 | 100 |
|  |  |  |  | 0.037 | 49 |
|  |  |  |  | 0.01 | 24 |
| 7 | H | H | " | 0.3 | 100 |
|  |  |  |  | 0.1 | 99 |
|  |  |  |  | 0.037 | 88 |
|  |  |  |  | 0.01 | 32 |
| 5 | (CO)CH₃ | H | p-OCH₃ | 0.3 | 99 |
|  |  |  |  | 0.1 | 80 |
|  |  |  |  | 0.037 | 22 |
| 5 | H | 4-CH₃, 6-CH₃ | H | 1 | 99 |
|  |  |  |  | 0.3 | 90 |
|  |  |  |  | 0.1 | 43 |
| 6 | H | H | p-OCH₃ | 0.3 | 100 |
|  |  |  |  | 0.1 | 79 |
|  |  |  |  | 0.03 | 45 |
| 7 | (CO)CH₃ | H | o-OCH₃ | 0.3 | 100 |
|  |  |  |  | 0.1 | 73 |
|  |  |  |  | 0.03 | 33 |
| 6 | H | 4-CH₃, 6-CH₃ | p-OCH₃ | 1 | 93 |
|  |  |  |  | 0.3 | 54 |
|  |  |  |  | 0.1 | 30 |
| 7 | H | H | m-OCH₃ | 0.3 | 100 |
|  |  |  |  | 0.1 | 100 |
|  |  |  |  | 0.03 | 76 |
| 7 | (CO)CH₃ | H | H | 0.1 | 100 |
|  |  |  |  | 0.037 | 95 |
|  |  |  |  | 0.01 | 40 |
| 5 | " | H | H | 0.3 | 100 |
|  |  |  |  | 0.1 | 97 |
|  |  |  |  | 0.037 | 58 |
| 7 | " | H | p-CN | 0.3 | 100 |
|  |  |  |  | 0.1 | 77 |
|  |  |  |  | 0.037 | 39 |
| 5 | " | H | p-OCH₃ | 0.3 | 100 |
|  |  |  |  | 0.1 | 60 |
| 7 | " | H | " | 0.1 | 100 |
|  |  |  |  | 0.037 | 59 |
| 7 | H | H | " | 0.1 | 100 |
|  |  |  |  | 0.037 | 24 |
| 5 | H | H | " | 0.3 | 100 |
|  |  |  |  | 0.4 | 63 |
| 7 | (CO)CH₃ | H | m-OCH₃ | 0.3 | 100 |
|  |  |  |  | 0.1 | 97 |
|  |  |  |  | 0.037 | 52 |
| 7 | H | H | H | 0.1 | 100 |
|  |  |  |  | 0.012 | 32 |
| 7 | (CO)CH₃ | 4-Cl | H | 1 | 100 |
|  |  |  |  | 0.1 | 32 |
|  |  |  |  | 0.037 | 22 |
| 7 | (CO)CH₃ | H | p-OCH₃ | 0.1 | 100 |
|  |  |  |  | 0.037 | 70 |
| 7 | (CO)CH₃ | 6-Cl | H | 1 | 100 |
|  |  |  |  | 0.3 | 82 |
|  |  |  |  | 0.1 | 63 |
| 4 | (CO)CH₃ | H | p-OCH₃ | 1 | 100 |
|  |  |  |  | 0.3 | 73 |
|  |  |  |  | 0.1 | 21 |
| 7 | H | t-Bu | H | 1 | 98 |
|  |  |  |  | 0.3 | 98 |
|  |  |  |  | 0.1 | 53 |
| 7 | (CO)CH₃ | t-Bu | H | 0.03 | 23 |
|  |  |  |  | 1 | 95 |
|  |  |  |  | 0.3 | 70 |
|  |  |  |  | 0.1 | 34 |

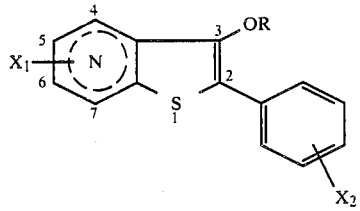

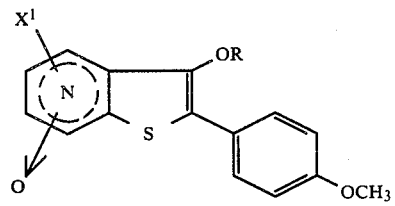

| Position of N | R | X₁ | X₂ | Dose mg/ml | % Inhibition |
|---|---|---|---|---|---|
| 7 | H | H | H | 1 | 98 |
|  |  |  |  | 0.3 | 94 |
|  |  |  |  | 0.1 | 39 |
|  |  |  |  | 0.03 | 0 |
| 7 | (CO)CH₃ | H | H | 1 | 95 |
|  |  |  |  | 0.3 | 55 |
|  |  |  |  | 0.1 | 31 |

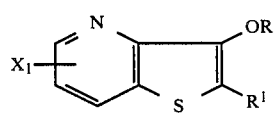

| Position of N | R | X₁ | Dose mg/ml | % Inhibition |
|---|---|---|---|---|
| 6 | (CO)CH₃ | H | 1 | 90 |
|  |  |  | 0.3 | 49 |
|  |  |  | 0.1 | 33 |

What is claimed is:

1. A compound which is 3-acetoxy-2-(4-methoxyphenyl)-4-azabenzo[b]thiophene.

2. A method for the treatment of a 5-lipoxygenase mediated disease comprising the administration to a mammalian species in need of such treatment an effective amouunt of a compound of formula (I):

or a pharmaceutically acceptable salt thereof wherein
R is (CO)CH$_3$; H; or loweralkyl;
R$^1$ is phenyl substituted with X$_2$;
X$_1$ is
  (a) H;
  (b) C$_{1-6}$alkyl;
  (c) halo;
  (d) halo-C$_{1-6}$alkyl;
  (e) CN;
  (f) —(CO)OR$^3$; or
  (g) —OC$_{1-6}$alkyl; and
X$_2$ is
  (a) H;
  (b) methylenedioxy;
  (c) haloC$_{1-6}$alkyl;
  (d) halo;
  (e) CN;
  (f) —OC$_{1-6}$alkyl,
  (g) —(CO)OR$^3$;
  (h) C$_{1-6}$alkyl; or
  (i) NO$_2$.

3. The method of claim 2 wherein the active compound is
3-acetoxy-2-(4-methoxyphenyl)-4-azabenzo[b]thiophene.

4. A pharmaceutical composition for treating a 5-lipoxygenase mediated disease in mammalian species comprising a pharmaceutically acceptable carrier and an effective amount of
3-acetoxy-2-(4-methoxyphenyl)-4-aza-benzo[b]thiophene or a pharmaceutically acceptable salt thereof.

* * * * *